United States Patent [19]
Wu

[11] Patent Number: 5,931,170
[45] Date of Patent: Aug. 3, 1999

[54] DENTAL FLOSSER

[75] Inventor: Ka Shing Wu, Kwun Tong, The Hong Kong Special Administrative Region of the People's Republic of China

[73] Assignee: Addway Engineering Limited, The Hong Kong Special Administrative Region of the People's Republic of China

[21] Appl. No.: 09/169,322

[22] Filed: Oct. 8, 1998

[51] Int. Cl.⁶ .................................................. A61C 15/00
[52] U.S. Cl. .......................................... 132/322; 433/118
[58] Field of Search .................................... 132/322, 328; 433/118, 143; 601/142

[56] References Cited

U.S. PATENT DOCUMENTS

| | | | |
|---|---|---|---|
| 4,820,153 | 4/1989 | Romhild et al. ........................ | 433/118 |
| 5,000,684 | 3/1991 | Odrich ..................................... | 433/118 |
| 5,573,020 | 11/1996 | Robinson ................................ | 132/322 |
| 5,700,146 | 12/1997 | Kucar ...................................... | 132/322 |
| 5,709,233 | 1/1998 | Boland et al. .......................... | 132/322 |
| 5,787,908 | 8/1998 | Robinason .............................. | 132/322 |

FOREIGN PATENT DOCUMENTS

| | | | |
|---|---|---|---|
| 706260 | 6/1931 | France .................................... | 433/118 |
| 4226649 | 2/1994 | Germany ................................ | 132/322 |

Primary Examiner—Todd E. Manahan
Attorney, Agent, or Firm—Miller, Sisson, Chapman & Nash, P.C.

[57] ABSTRACT

A dental flosser has a bushing with a lateral pin that engages in a spiral groove in a sleeve that surrounds the bushing. The bushing is driven backwards and forwards by a shaft and this causes a flosser element base anchor to be rotated clockwise and counterclockwise, and moved backwards and forwards at the same time during use.

5 Claims, 3 Drawing Sheets

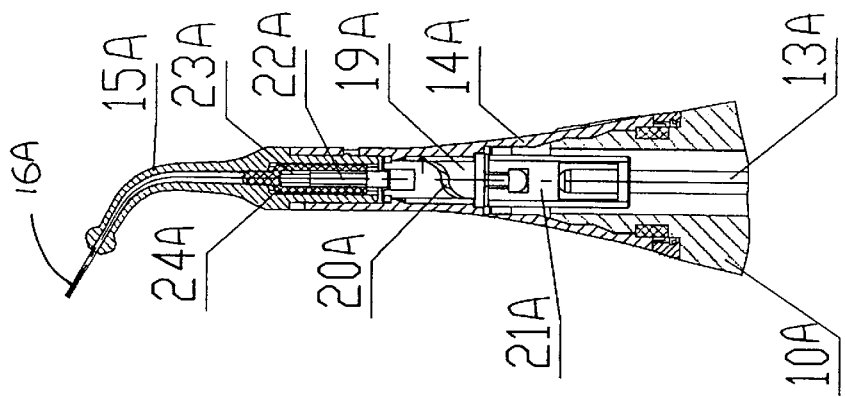
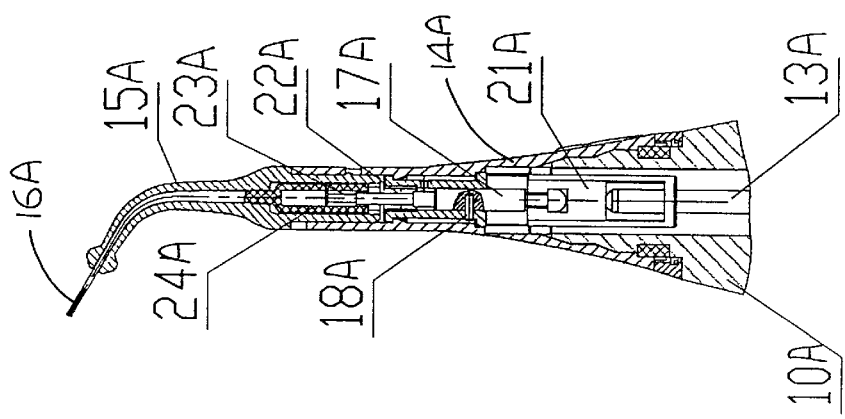

DENTAL FLOSSER

The invention relates to dental flossers.

BACKGROUND OF THE INVENTION

It is known to provide dental flossers that are driven by an electric motor to rotate about a longitudinal axis of a flosser element.

SUMMARY OF THE INVENTION

It is an object of the invention to provide an improved motor-driven dental flosser.

According to the invention there is provided a dental flosser comprising a flosser element arranged to be drivingly connected to a drive head member, in which the drive head member is arranged to convert a reciprocating drive from a drive shaft of an electric motor into clockwise and counter-clockwise rotational motion for rotating the flosser element.

Preferably, the drive head member is arranged to convert the reciprocating drive into forwards and backwards and clockwise and counterclockwise rotational motion for pushing and pulling and rotating the flosser element.

A flosser element holder for the flosser may comprise a cranked channel in which the flosser element can rotate and/or slide in use.

The drive head member may include a bushing with a laterally extending pin, a cylindrically sleeve that surrounds the bushing and is formed with a spiral groove in its inner surface to engage the pin, such that inter-engagement causes the bushing to be rotated as it is moved forwards and backwards within the sleeve.

A splined shaft may be provided that extends from one end of the bushing to slidingly engage with a flosser element anchor.

The flosser element holder is preferably arranged to be readily attachable and removable from the drive head member.

The dental flosser may include a handle incorporating an electric motor and reciprocal drive arrangement, in which the drive head member is arranged to be readily attachable and removable from the handle.

BRIEF DESCRIPTION OF DRAWINGS

A dental flosser according to the invention will now be described, by way of example only, with reference to the accompanying drawings in which:

FIG. 4 is a cross-sectional side view of an alternative flosser attachment, shown in one operating condition; and FIG. 5 is a cross-sectional side view of the flosser attachment of FIG. 4, shown in another operating condition.

DETAILED DESCRIPTION OF PREFERRED EMBODIMENTS

Figure 1:
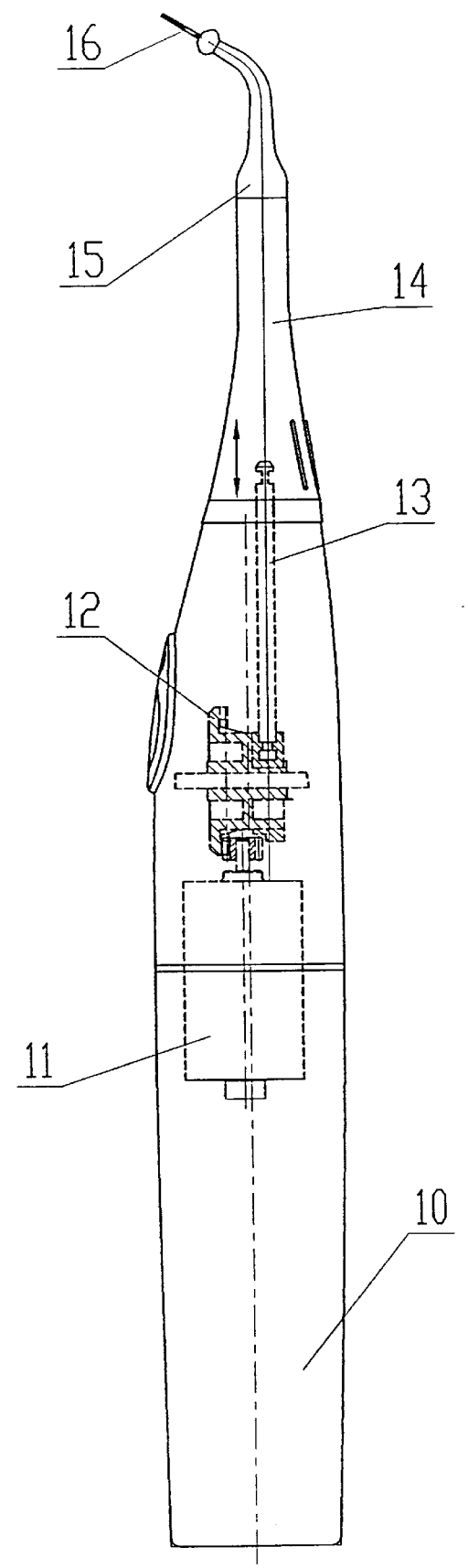
FIG. 1 is a schematic side view of a complete flosser embodying the invention, including a flosser attachment.

Referring to the drawings, in FIG. 1 the flosser comprises a handle 10 having an electric motor 11, a drive mechanism 12 and a battery, all mounted inside the handle 10. A drive output shaft 13 is arranged to be reciprocated forwards and backwards (i.e. upwards and downwards in the Figure) by the motor 11. A flosser head drive member 14 has one end fitted to the handle 10 and another end fitted to a flosser element holder 15, said parts 14 and 15 constituting a flosser attachment. An end of a flosser element 16 is arranged to move in and out of a remote end of the flosser element holder 15, in use, and to be turned clockwise and counterclockwise, respectively, as it does so.

Figure 3:
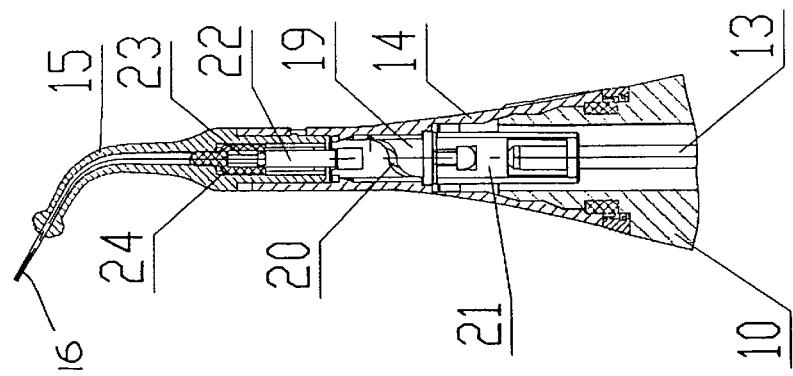
FIG. 3 is a cross-sectional side view of the flosser attachment of FIG. 2, with the flosser element in an extended position.
Figure 2:
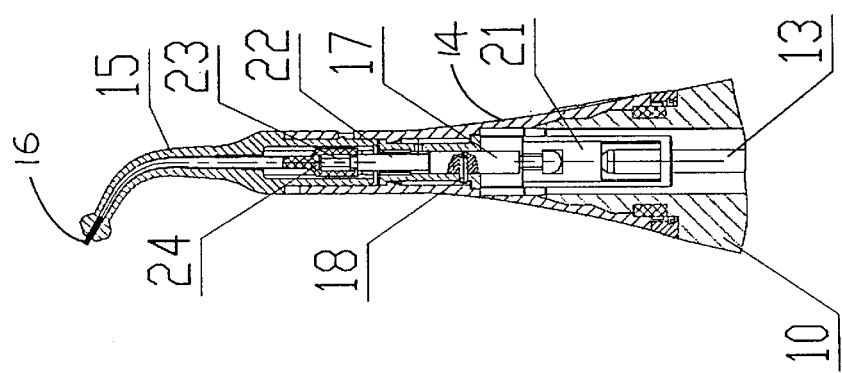
FIG. 2 is a cross-sectional side view of the flosser attachment of FIG. 1, with a flosser element in a retracted position.

In FIGS. 2 and 3, the flosser head drive member 14 has a bushing 17 in which a pin 18 is mounted that extends laterally out of the bushing 17. A cylindrical sleeve 19 with a spiral groove 20 surrounds the bushing 17 and the pin 18 fits slidably into the spiral groove 20. A mechanical coupling 21 connects an upper end of the shaft 13 to a lower end of a central shaft 22, around which shaft 22 the bushing 17 is integrally formed. The shaft 22 extends upwards to a splined end 23 which is fixed into the lower end of a flosser element base anchor 24 slidable axially within the flosser element holder 15.

As the shaft 22 is driven forwards and backwards by the motor 11, the inter-engagement between the pin 18 and the groove 20 causes rotation of the shaft 22 and the base anchor 24. Thus, the base anchor 24 is driven forwards and backwards and rotated clockwise and counterclockwise respectively at the same time.

The flosser element holder 15 has a crooked or cranked channel as shown, along which the flosser element 16 can slide and within which the flosser element 16 can rotate. The cranked shape makes the flosser element 16 more easy to position and to manipulate in a user's mouth during use.

The flosser head drive member 14 and the flosser element holder 15 are push-fits to the handle 10 and to each other respectively. This allows the parts to be removed for cleaning and also allows the handle 10, with its motor 11, to be fitted to other attachments, for example a tooth brushing attachment (as described in U.S. Pat. No. 5,617,601). The flosser element base anchor 24, with the flosser element 16, are in any event likely to be replaced in practice quite frequently by a new base anchor 24 with flosser element 16, as required.

FIGS. 4 and 5 show an alternative flosser attachment which has a similar construction and operates in a slightly different way, with like parts designated by the same reference numerals suffixed by a letter "A". The only major differences lie in the flosser element base anchor 24A being made longer and not slidable within the flosser element holder 15A to have the flosser element 16A extending out of the holder 15A all the time, and in the splined end 23A of the shaft 22A being made slidable axially within the base anchor 24A.

In this arrangement, the forward and backward motion of the shaft 22A will not be transferred to the base anchor 24A but only its rotational motion, thereby causing the base anchor 24A and in turn the flosser element 16A to rotate clockwise and counterclockwise only. While always extending out, the flosser element 16A may easily be positioned for insertion into the gaps between the user's teeth.

The invention has been given by way of example only, and various other modifications of and/or alterations to the described embodiment may be made by persons skilled in the art without departing from the scope of the invention as specified in the appended claims.

I claim:

1. A dental flosser comprising a flosser element drivingly connected to a drive head member, said drive head member having a means for converting a reciprocating drive from a drive shaft of an electric motor into clockwise and counterclockwise rotational motion for rotating said flosser element, said converting means comprising a bushing with a laterally extending pin, a cylindrical sleeve that surrounds said bushing, a spiral groove in an inner surface of said bushing to engage said pin such that inter-engagement causes said bushing to be rotated as it is moved forwards and backwards within said sleeve.

2. A dental flosser according to claim 1, further comprising a flosser element holder having a cranked channel in which said flosser element can rotate and slide in use.

3. A dental flosser according to claim 1, further comprising a splined shaft extending from one end of said bushing to slidingly engage with a flosser element anchor.

4. A dental flosser according to claim 1, wherein said flosser element holder is readily attachable and removable from said drive head member.

5. A dental flosser according to claim 1, further comprising a handle incorporating said electric motor and said reciprocal drive wherein said drive head member is readily attachable and removable from said handle.

* * * * *